US010722281B2

(12) United States Patent
Boboltz (10) Patent No.: US 10,722,281 B2
(45) Date of Patent: *Jul. 28, 2020

(54) ACCESS CANNULA WITH LEAKAGE PREVENTION VALVE (71) Applicant: Stryker Corporation, Kalamazoo, MI (US)

(72) Inventor: David Robert Boboltz, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/119,230

(22) Filed: Aug. 31, 2018

(65) Prior Publication Data

US 2018/0368900 A1 Dec. 27, 2018

Related U.S. Application Data (63) Continuation of application No. 14/923,873, filed on Oct. 27, 2015, now Pat. No. 10,092,342, which is a continuation of application No. PCT/US2013/038757, filed on Apr. 30, 2013.

(51) Int. Cl.
*A61B 17/88* (2006.01)
*A61B 17/34* (2006.01)

(52) U.S. Cl.
CPC ...... *A61B 17/8819* (2013.01); *A61B 17/8816* (2013.01); *A61B 17/8833* (2013.01); *A61B 17/3462* (2013.01); *A61B 17/3472* (2013.01); *A61B 17/3498* (2013.01); *A61B 2017/8838* (2013.01)

(58) Field of Classification Search
CPC ............... A61B 17/8819; A61B 17/3498
See application file for complete search history.

(56) References Cited

U.S. PATENT DOCUMENTS

| | | | |
|---|---|---|---|
| 4,177,814 A | 12/1979 | Knepshield | |
| 6,547,432 B2 | 4/2003 | Coffeen et al. | |
| 7,399,306 B2 | 7/2008 | Reiley et al. | |
| 7,658,537 B2 | 2/2010 | Coffeen et al. | |
| 10,092,342 B2 | 10/2018 | Boboltz | |
| 2003/0105469 A1 | 6/2003 | Karmon | |
| 2003/0167040 A1 | 9/2003 | Bacher et al. | |
| 2007/0260258 A1 | 11/2007 | Sommerich | |
| 2008/0009792 A1 | 1/2008 | Henniges et al. | |
| 2010/0094269 A1 | 4/2010 | Pellegrino | |

OTHER PUBLICATIONS

PCT "International Search Report and Written Opinion" for PCT/US2013/038757, dated Jan. 2014.

*Primary Examiner* — Andrew Yang
(74) *Attorney, Agent, or Firm* — Howard & Howard Attorneys PLLC

(57) ABSTRACT

An access cannula that defines a portal to the tissue to which the material is delivered. The access cannula includes a valve. The valve prevents the flow of material out of the access cannula. The valve also prevents the pressure head at the site at which the access cannula is inserted from forcing a delivery cannula out of the access cannula.

17 Claims, 8 Drawing Sheets

ACCESS CANNULA WITH LEAKAGE PREVENTION VALVE

RELATIONSHIP TO EARLIER FILED APPLICATIONS

This application is a continuation of U.S. patent application Ser. No. 14/923,873, filed on Oct. 27, 2015, which is a continuation of PCT Pat. App. No. PCT/US2013/038757 filed Apr. 30, 2013. The contents of the above-listed priority applications are incorporated herein by reference.

BACKGROUND OF THE INVENTION

There are a number of different medical conditions in which the course of treatment involves the injection of cement into the hard tissue, the bone of the patient. One such procedure is a vertebroplasty procedure. In a vertebroplasty procedure bone cement is injected into a vertebra that was previously fractured. The procedure is performed to stabilize fractured vertebra. The procedure is performed to reduce the undesirable effects of the fracture. These effects are known to include, back pain, spinal deformity and loss of patient height.

In a vertebroplasty procedure and other procedures in which cement is injected into bone an assembly that consists of at least two cannulae is often employed to inject the cement. The first one of the cannula is an access cannula. The access cannula is used to define a portal from the outside environment, through soft tissue that surrounds the bone and into the bone into which the cement is to be injected. The assembly includes one additional cannula, referred to as a delivery cannula or cement cannula. The delivery cannula is dimensioned to be inserted into the lumen of the access cannula.

To actually deliver the bone cement the access cannula is first inserted into the patient. Often during the positioning process a pointed tip stylet is seated in the lumen of the access cannula. The tip of the stylet is the component of the assembly that pierces the tissue through which the cannula is inserted. The access cannula is positioned so the end of the cannula is positioned at the location in bone in which the cement is to be introduced. In some bone cement procedures a device is used to widen out space around the distal end of the access cannula. This is step is performed to ensure the presence of a void space into which the cement can flow. A previously filled delivery cannula is then seated in the access cannula. An obturator, a type of a plunger is then employed to force the bone cement out of the delivery cannula into the space into which the cement is to be introduced.

To minimize the trauma to the patient and to facilitate the precise control of the discharge of bone cement, both the access cannula and delivery cannula are relatively small in size. For example an access cannula often has an outer diameter of 5 mm or less. By extension that means that the inner diameter of the delivery cannula, the diameter of the lumen internal to the delivery cannula is 3.5 mm or less. This means that the volume of cement contained in any given filed delivery cannula is often 2 cm3 or less. Often a procedure in which it is necessary to inject bone cement into a patient requires a volume of cement that is greater than the volume contained in any one delivery cannula. This is why at the start of the procedure the practitioner has available two or more delivery cannula. Once the cement is discharged from one delivery cannula, the practitioner withdraws that cannula from the access cannula. A replacement delivery cannula filled with cement is then inserted into the cannula. Once the newly filled delivery cannula is in place, the part of the procedure in which the cement is actually injected into the bone can continue.

A problem during the cement injection procedure has been known to occur during the time period between the withdrawal of one delivery cannula from the access cannula and the insertion of a second access cannula. Specifically, during this time period, the access cannula, which is then empty, is known to fill with blood. This fluid is known to leak out of the proximal back end of the access cannula. To prevent this fluid leakage and the subsequent need to clean this fluid, the current practice is for the practitioner to, as soon as he/she removed the withdraws a delivery cannula, place a thumb or finger over the open proximal end of the cannula. This digit must be carefully positioned so as to not cause the movement of the access cannula. Having to hold the access cannula while putting away the empty delivery cannula and fitting a filled delivery cannula back into the access tube can make the removal and refitting of these cannulae an ergonomically awkward experience.

SUMMARY OF THE INVENTION

This invention relates to a new and useful assembly for injecting a substance such as bone cement into a living being. This assembly typically includes both an access cannula and a delivery cannula. The assembly of this invention is designed to minimize the leakage of fluid from the assembly during time periods when another component of the assembly is not disposed in the access cannula.

The access cannula of this invention includes a valve. Specifically, the valve of this invention allowed insertion and withdrawal of a delivery cannula. When a delivery cannula or other device is not seated in the access cannula, the valve blocks the flow of fluid out of the access cannula.

In many versions of this invention the valve and access cannula are further constructed to apply a restraining force on the delivery cannula when the delivery cannula is withdrawn from the access cannula. This restraining force substantially eliminates the likelihood that the presence of a pressure head at the site to which the assembly is applied can force the delivery cannula out of the access cannula.

In some versions of the invention, the valve has one or more valve flaps formed from elastomeric material. In some alternative versions of the invention, the valve may include another valve element formed from elastomeric material. Alternatively, the valve may have a biasing spring or springs that hold the valve flaps in the closed state.

A more specific version of this invention is used to deliver bone cement into a bone such as a vertebral body. This version of the invention includes a bone cement mixing assembly. As the name implies, this assembly produced bone cement. The delivery cannula of this version of this invention, sometimes referred to as a delivery cannula, is adapted to be releasably secured to an outlet fitting of the mixing assembly. Once the bone cement is prepared the cement is loaded into the delivery cannula. The delivery cannula is then fitted into the positioned access cannula. An obturator is inserted through the delivery cannula to push the cement out into the space internal to the bone at which the cement is to be delivered.

Some assemblies of this invention do not include the delivery cannula. In these versions of the invention, the valve internal to the access cannula is again normally closed. In these versions of the invention, the insertion of a stylet, the injection of cement or the insertion of an obturator into the lumen of the access cannula provides sufficient force to overcome the force of the valve that holds the valve closed. The withdrawal of either the stylet or obturator, or terminating of the force applied to the cement for injection purposes results in the valve closing. The pressure head of fluid that flows proximally from the open distal end of the access cannula does not provide sufficient force to urge the valve into the open state.

BRIEF DESCRIPTION OF THE DRAWINGS

The invention is pointed out with particularity in the claims. The above and further features and benefits of this invention are understood from the following Detailed Description taken in conjunction with the following drawings in which:

DETAILED DESCRIPTION

Figure 1:
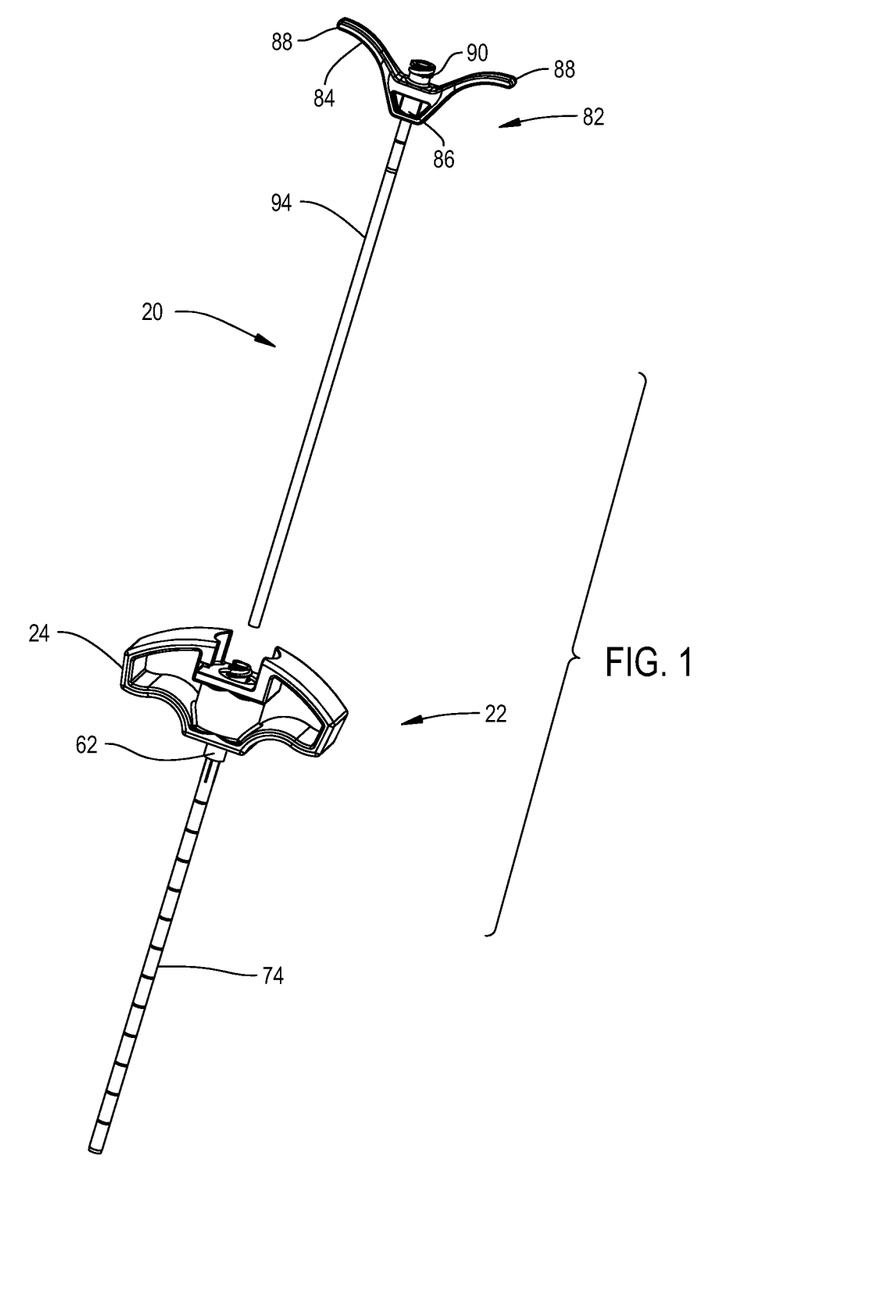
FIG. 1 is an exploded view of the components of the delivery system of this invention.

FIG. 1 illustrates a delivery assembly 20 of this invention useful for introducing fluid and semisolids into living tissue. Often assembly 20 of this invention is employed to deliver bone cement. Assembly 20 includes an access cannula 22 and a delivery cannula 82. The access cannula 22 is used to form a portal that leads to the location internal to the patient at which the material is to be introduced. The delivery cannula 82 is dimensioned to be slidably and removably disposed in the access cannula 22. Prior to insertion of the delivery cannula 82 into the access cannula 22, the delivery cannula is filled with the material to be introduced into the tissue. Once the delivery cannula 82 is seated in the access cannula 22 an obturator is used to force the material out of the delivery cannula into the tissue.

Figure 2:
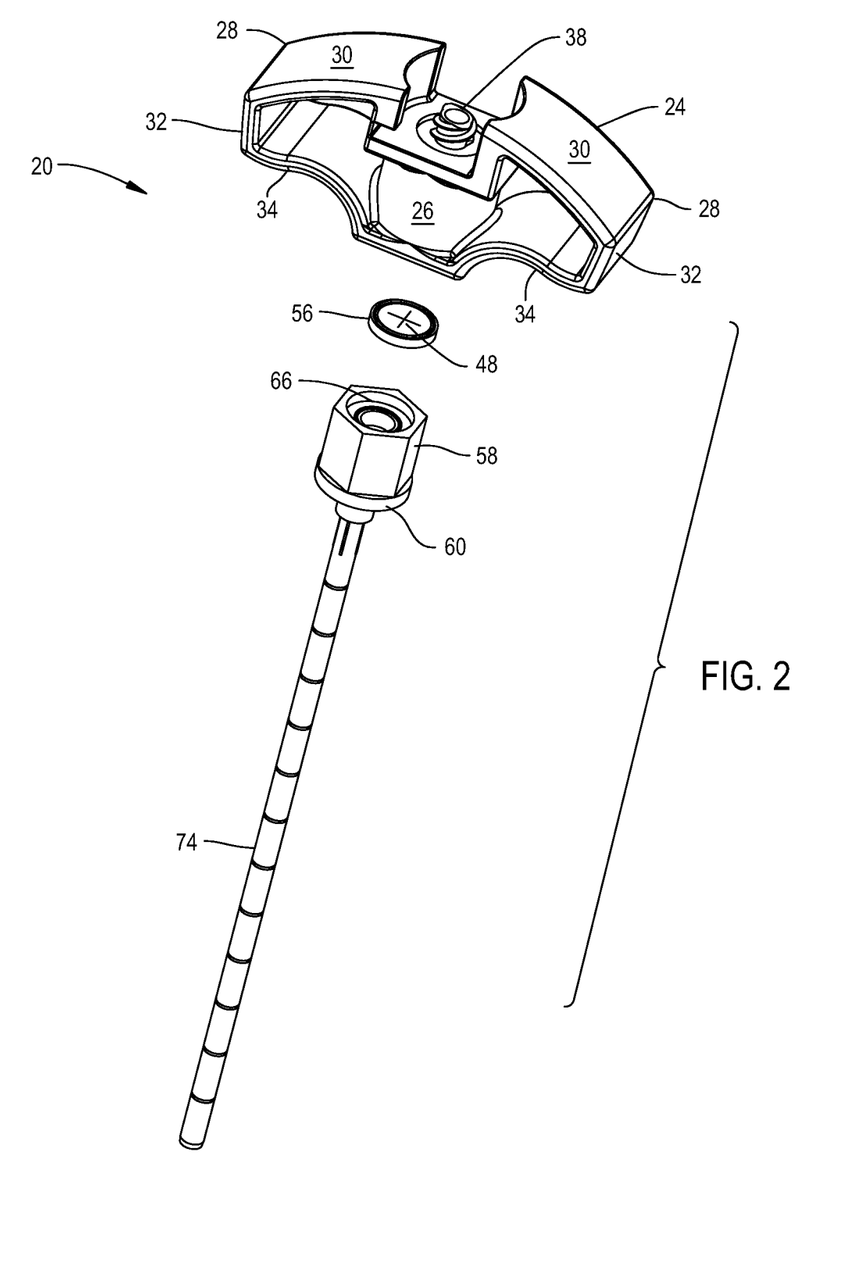
FIG. 2 is an exploded view of the components forming the access cannula.
Figures 3, 4:
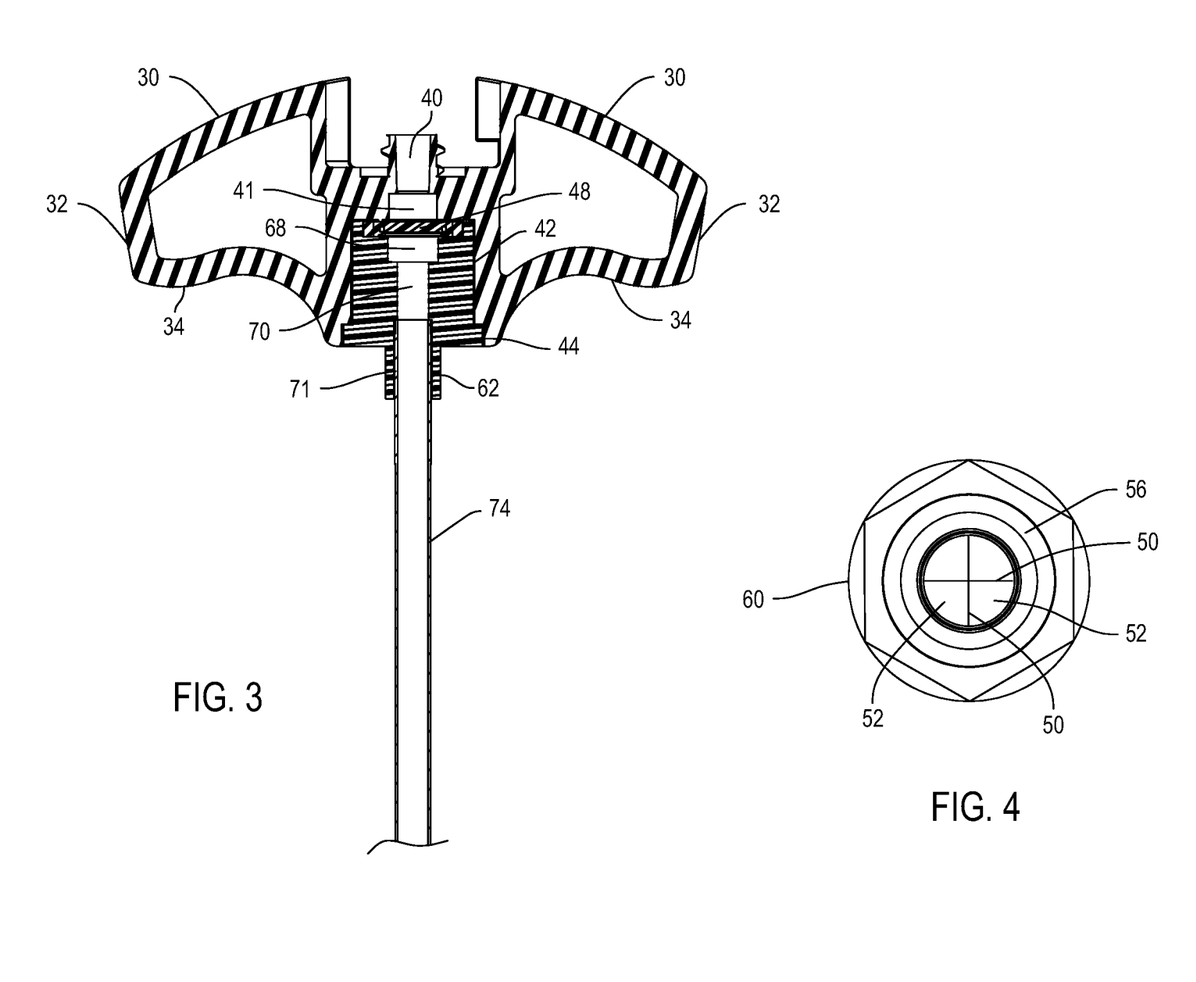
FIG. 3 is a cross sectional view of the proximal end of the access cannula.
FIG. 4 is a plan view looking distally forward of the hub and valve of the access cannula.

Access cannula 22, as seen best in FIGS. 2-4, includes a handle 24. Handle 24 is a single piece unit that includes a base 26. In the depicted version of the invention, base 26 has a cylindrical outer wall. Two finger grips 28 extend outwardly from the opposed sides of the base 26. Each finger grip 28 includes a beam 30 that extends outwardly from the base 26 adjacent the proximal end of the base. (Here "proximal" is understood to mean towards the practitioner holding the access cannula 22, away from the tissue to which the cannula is to be directed. "Distal" is understood to mean away from the practitioner, towards the tissue to which the cannula 22 is to be directed.) A beam 34, located below the beam 30, extends outwardly away from the base 26 adjacent the distal end of the base. A web 32 extends between the free ends of the beams 30 and 34.

A fitting 38 with threading (not identified) extends upwardly from the center of proximally directed face of handle base 26. Fitting 38 has a lumen 40. Handle 24 is formed so that lumen 40 extends a short distance into handle base 26. Fitting lumen 40 opens into bores 41 and 42 that are coaxial with the lumen and within the handle base 26. Bore 41 has a diameter approximately 2 mm greater than that of lumen 40. Bore 42 has a diameter approximately 9 mm greater than that over bore 41. In terms of overall length, bore 42 extends at least 50% of the distance through the handle base 26. In some versions of the invention, bore 42 is in the form of a polygon. In still more particular versions of the invention, bore 42 is in the form of a hexagon. A counterbore 44, coaxial with bore 42, forms the open distal end of handle base 26. Counterbore 44 is circular in cross section.

A valve 48 is seated in the proximal end base of bore 42, where the fitting bore 41 opens into bore 42. Valve 48 as seen best in FIGS. 2 and 4, is the form a disc shaped piece of rubber. The valve 48 has a thickness of between 0.5 and 3.0 mm. Valve 48 is formed to have two slits 50 that are perpendicular to each other and that cross at the center of the valve. Slits 50 define valve flaps 52, only two flaps identified.

In the illustrated version of the invention, valve 48 is encased in a ring 56. Ring 56 is often formed from nylon or other plastic and has a wall thickness of between 1 and 4 mm. In some methods of manufacturing assembly 20, after ring 56 is molded, valve 44 is molded within the ring 52. Once the valve 44 is formed, the flap-defining slits 46 are formed.

Also disposed in handle bore 42 is a hub 58 that is formed from nylon or other plastic. Hub 58 has a body, (not identified) that has a cross sectional shape that allows the hub to be press fit in bore 42. In the depicted version of the invention, the hub body has a shape in cross section that is hexagonal. At the distal of the body a rim 60 extends radially outwardly from the hub body. Rim 60 is designed to press fit in handle counterbore 44. A sleeve 62 extends outwardly from the distally directed face of the hub. Hub 58 has a length such that when the hub is mounted to handle 24, the distally directed face of the hub is flush with the handle and sleeve 62 extends forward from the handle.

A number of bores form a through channel that extends longitudinally through hub 58 along the longitudinal axis through the hub. A first bore, bore 66, extends distally from the proximal end of hub 58. Bore 66 has a diameter that facilitates the press fitting of ring 56 in the bore 66. Bore 66 has a depth such that when the ring 56 is disposed in the bore, the ring is flush with the proximally directed face of hub 58. Bore 66 opens into a bore 68. Bore 68 has a diameter that is less than the diameter of bore 66. In many versions of the invention hub bore 68 has the same diameter as handle base bore 41. Bore 68 opens up into a bore 70. Bore 70 is smaller in diameter than bore 68. Bore 70 opens up into a bore 71. Bore 71 is the distalmost bore of the hub 58. Bore 71 forms the lumen through sleeve 62.

A tube 74, that forms the actual body of the access cannula 22, extends proximally from the hub 58. Tube 74, being the body of the access cannula 22, is the component of the cannula 22 that is inserted into the patient. The tube 74 is formed from stainless steel or other material capable of being inserted into living tissue. Tube 74 has an outer diameter of typically 5 mm or less and often 3.5 mm or less. Tube 74 has a wall thickness of 0.5 mm. Tube 74 is seated in hub bore 71 and extends through and forward of sleeve 62.

In some versions of manufacturing the access cannula 22, hub 58 is overmolded over tube 74. This overmolded thus forms hub 71. Once the hub and tube sub-assembly is formed, the ring and valve assembly is press fit in bore 66. Hub 58 with the components attached thereto, is then press fit in handle bore 42. The process of fitting the hub 58 and attached components to the handle 24.

Returning to FIG. 1, it is seen that the delivery cannula 82 includes a handle 84. The handle 84 includes a base 86 from which two opposed wings 88 extend. A fitting 90 extends proximally outwardly from the proximal face of base 86. Fitting 90 is formed with features that facilitate the attachment of fitting to a mixer in which the cement is held prior to being loaded in the delivery cannula.

Figure 5:
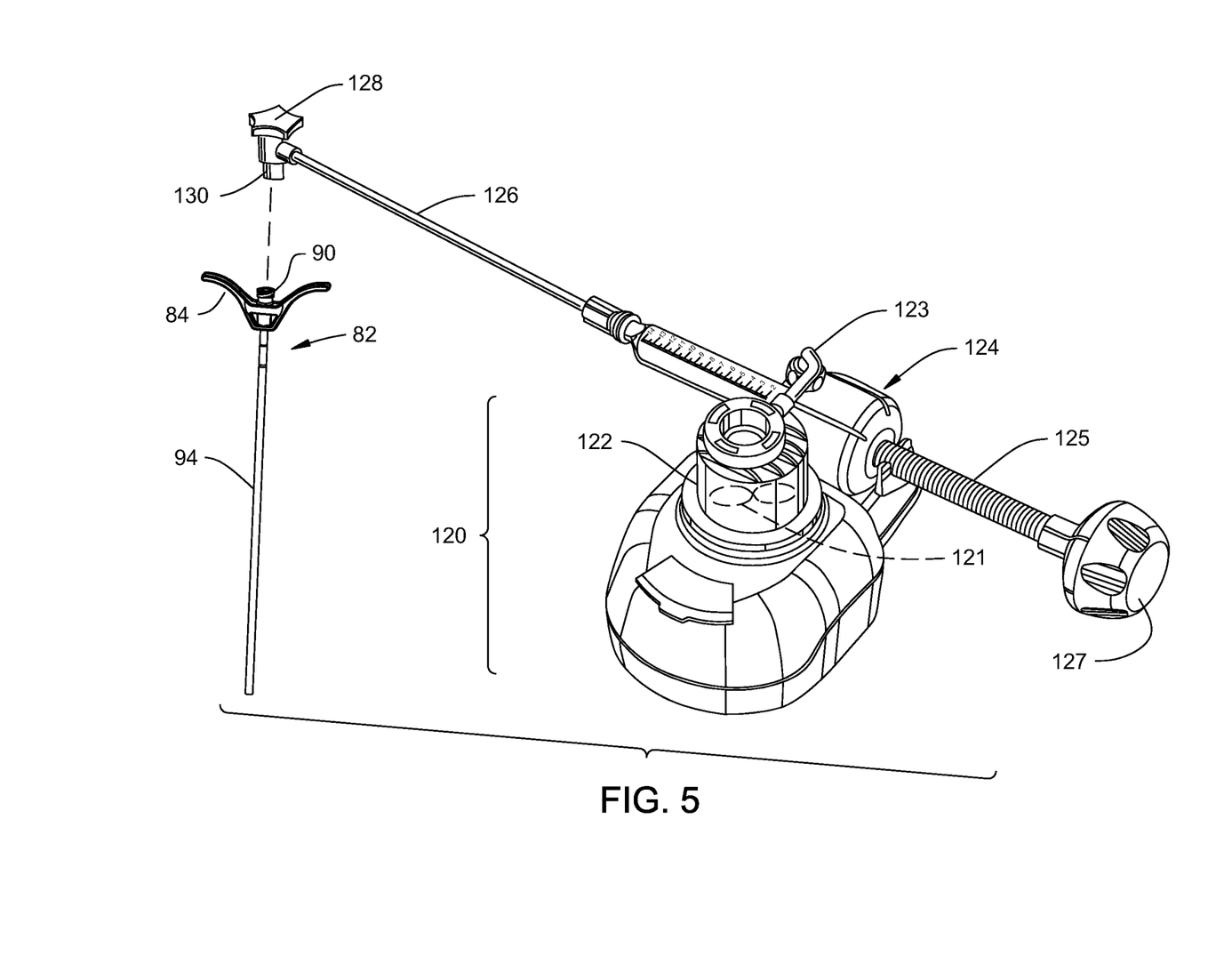
FIG. 5 is an exploded view depicting how the delivery cannula of this assembly, sometimes referred to as a delivery cannula, is attached to a bone cement mixer.

One such cement mixer 120 that can be incorporated into this invention is seen in FIG. 5. Mixer 120 includes a first chamber 122 in which the material to be filled in the cannula is mixed. Not seen is the paddle disposed in chamber 122 that mixes the components forming the cement together to form the cement. Mixer 120 also includes a second chamber 124 into which the material is initially flowed after mixture. Not identified is the tube that extends from the first chamber 122 to the second chamber through which the mixed cement is flowed to the second chamber 124. An extension tube 126 extends from the second chamber 124. An outlet fitting 130 is attached to the distal end of the extension tube 126. Mixer outlet fitting 130 has the features that engage the fitting 90 integral with the delivery cannula 82. These features are configured to facilitate the releasable engagement of the delivery cannula to the mixer 120. In the depicted version of the invention a valve 128 controls fluid flow through mixer outlet fitting 128. The Applicant's U.S. Pat. No. 6,547,432 issued 15 Apr. 2003, and U.S. Pat. No. 7,658,537 issued 9 Feb. 2012, each of which is incorporated herein by reference, provide further description of the construction of cement mixers. It should be understood that the exact structure cement mixer that may be integrated into this invention is not part of the present invention.

Returning to FIG. 1 it can be understood that delivery cannula 82 includes a tube 94 that extends distally forward from handle 84. Tube 94 has an outer diameter that allows the tube 94 to slip fitting in access cannula fitting 38 and the lumen of access cannula tube 74. In many versions of the invention, the lumen internal to tube 94 (lumen not identified) has a volume of 2 cm3 or less, typically 1.5 cm3 or less and sometimes 1.0 cm3 or less.

In many versions of the invention, handle 84 is overmolded over tube 94 to form the delivery cannula 82.

Delivery assembly 20 of this invention is prepared for use by filing the tubes 94 of one or more delivery cannulae 82 with the material that is to be introduced into the living tissue. FIG. 5 depicts the filling of a single delivery cannula 82 from cement mixer 120. When assembly 20 of this invention is used to inject bone cement into tissue, the delivery cannula 82 is sometimes referred as a cement cannula.

A stylet is fitted in the access cannula 22. The tip of the stylet extends forward of the distal end of cannula tube 74. The access cannula and stylet are inserted into the patient. The access cannula 22 is positioned so that the distal end of the cannula is positioned adjacent the location where the fluid or semi-solid to be introduced. The stylet is removed. A void creation tool, such as a balloon may then be inserted in the cannula. This tool, which is not part of the present invention, is used to create a void space into which the fluid, semi-solid or other material to be introduced. The device is withdrawn from the cannula.

Figure 6:
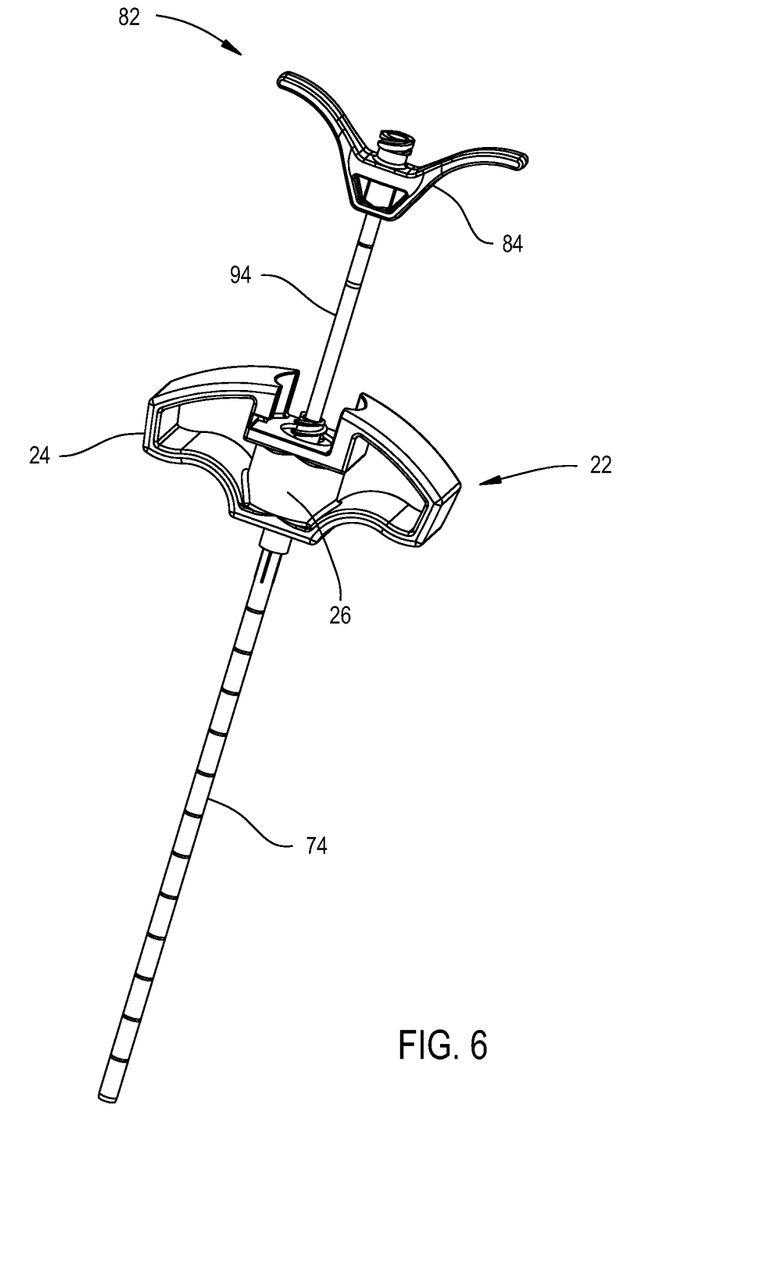
FIG. 6 is a perspective view of the insertion of the delivery cannula, sometimes specifically referred to as the delivery cannula, inserted into the access cannula.

A delivery cannula is then inserted in the access cannula as seen in FIG. 6. More specifically the delivery cannula 82 is positioned so that delivery cannula tube 94 seats in access cannula tube 74. An obturator or other plunger like device is then inserted in the access cannula tube 84. This device forces the material in the delivery cannula tube 94 out of the cannula and into the tissue in which the material will have a therapeutic benefit.

During the period of time in which there is neither a void-creating device nor a delivery cannula 82 in the access cannula 24, the flaps 52 of valve 48, abut. The flap-against flap contact blocks the flow of fluid present in the empty access cannula tube 74 out through the cannula fitting 38. When a stylet, a void creation tool or a delivery cannula 82 is inserted in the access cannula, the flaps are flexed downwardly, into the outer annular portion of hub bore 68. Thus the presence of the flaps does not impede the insertion of the device inserted into the access cannula through either the hub 58 or cannula tube 74.

The valve flaps are formed from elastomeric material, material that, upon the removal of a deforming force, returns to its undeformed state. Accordingly once the device is removed from the access cannula 22, the valve flaps 52 flex back to the abutting, closed valve, state. Valve 44 prevents flow of liquid that may enter access cannula tube 74 from percolating up and out of the access cannula fitting 38. Thus, during time periods when there is neither a stylet, a void creation tool or a delivery cannula disposed in the access cannula, the assembly of this invention inhibits the unwanted discharge of fluid out of the access cannula 22. This means that during these time periods of procedure, neither the practitioner nor an assistant need to hold a thumb or finger over access cannula fitting 38 to prevent such discharge. This frees the individual having to perform this task so he/she can concentrate on other aspects of the procedure.

It is a further feature of the assembly 20 of this invention that the valve 44 automatically opens upon the insertion of the complementary device in the access cannula 22. Valve 44 likewise automatically closes upon withdrawal of the device from the access cannula 22. This means that the assembly of this invention eliminates the undesirable discharge of fluid without requiring the medical personnel to take any additional steps.

The assembly of this invention does more than just prevent fluid flow out of the access cannula when a first delivery cannula is withdrawn and a new delivery cannula put in position. The valve prevents blood loss out of the access cannula in the time period between when the void creation tool is withdrawn from the access cannula and a delivery cannula inserted into the access cannula. In practice it has been found that in a procedure in which two access cannulae are simultaneously inserted into a patient, the creation of void space adjacent a first one of the cannula results in a build up of pressure adjacent the distal end of the second access cannula. This pressure build up forces fluid, primarily blood, through the access cannula 22. If neither a stylet, a void creation tool nor a delivery cannula is disposed in the second access cannula, the valve limits, if not blocks the flow of this fluid out of the proximal end of the second access cannula.

Figure 7:
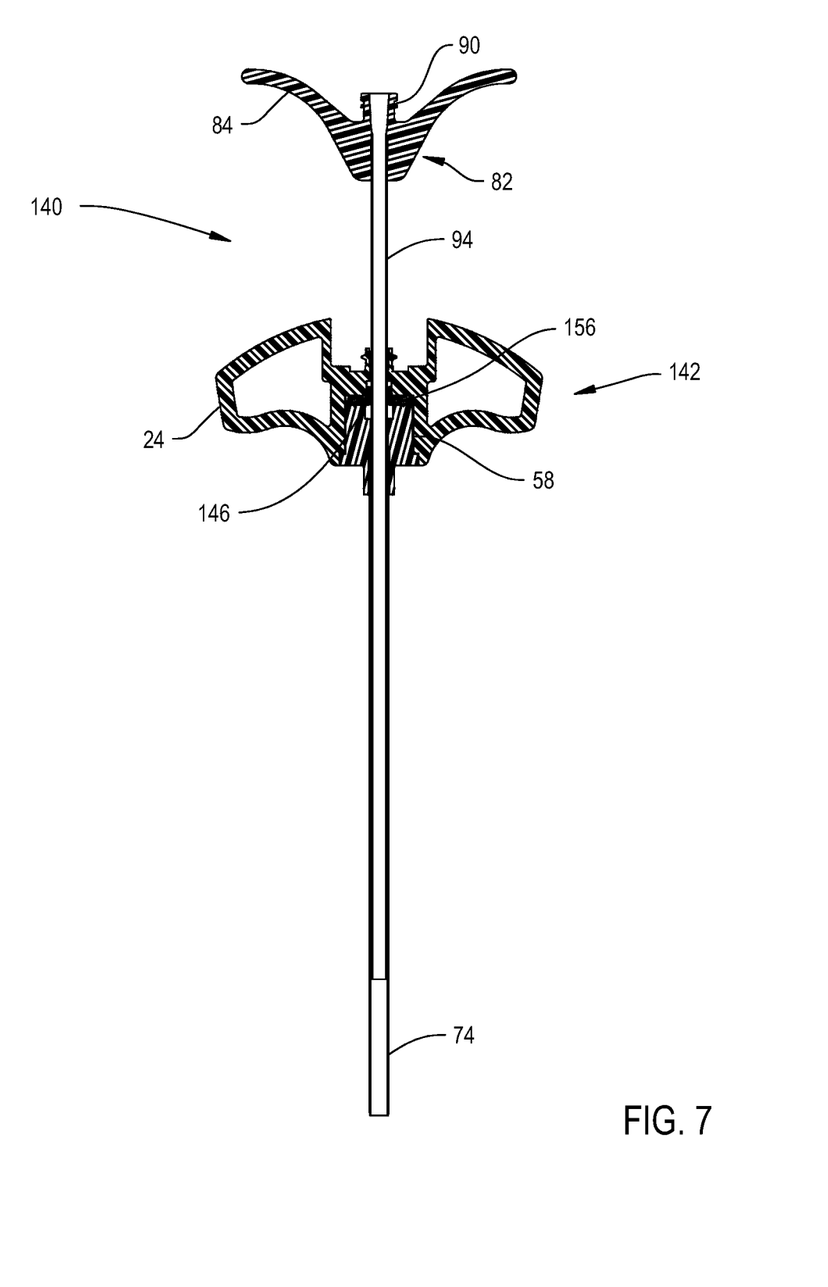
FIG. 7 is a cross sectional view of an alternative delivery assembly of this invention.
Figure 7A:
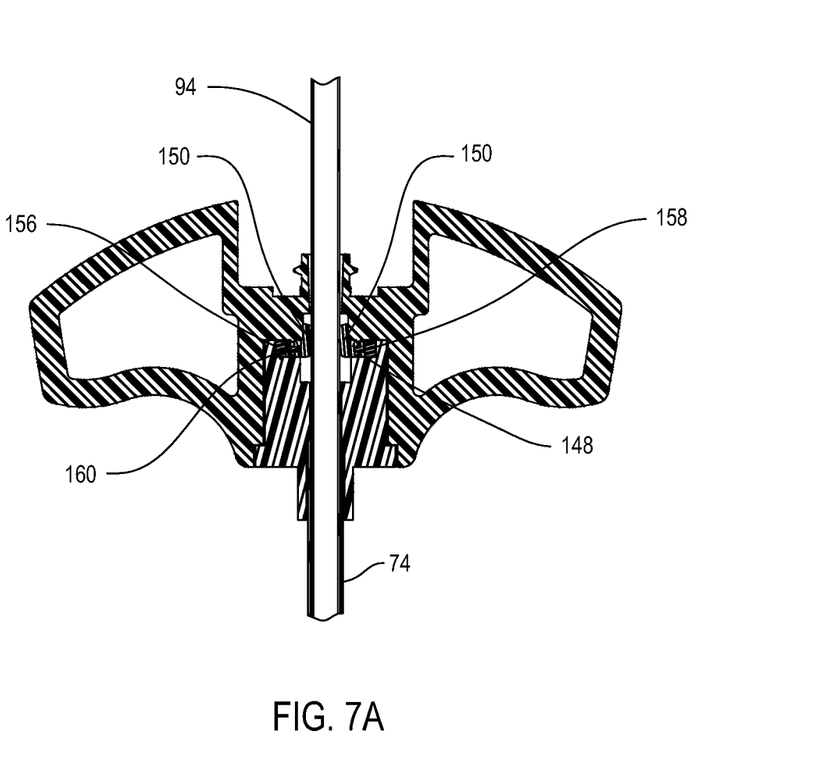
FIG. 7A is an enlarged view of a portion of the cross sectional view of FIG. 7.

FIGS. 7 and 7A illustrate an alternative delivery assembly 140 of this invention. delivery assembly includes access cannula 142 and the previously described delivery cannula 82. Many of the components of access cannula 142 are similar to those of the first described access cannula 22 accordingly these components will not be redescribed.

Instead of valve 48 and ring 56, access cannula 142 includes a valve 146 and a ring 156. Valve 146 is formed from the same material from which valve 48 is formed. Valve 48 is disc shaped. The valve 146 is further formed to have a groove 148 that extends inwardly from the circular side surface of the valve. Groove 148 extends circumferentially around the valve 146. While not identified, valve 146 is formed with slits similar to slits 50 of valve 48. These slits separate the center portion of the valve 146 into flexible flaps 150.

In this version of the invention, the components forming the assembly 140 are constructed so that the radius of delivery cannula tube 94 and the thickness of a valve flap 150 is approximately 0.5 mm greater than the radius of bore 41 internal to access cannula fitting 38. The reason for this dimensioning is apparent below.

Ring 156 is formed from the same material from which ring 56 is formed. Ring 156 has a circular main body 158 similar to the body of ring 56. The ring 156 is further formed to have a lip 160 that extends inwardly from the cylindrically shaped inner surface of the main body 160. Ring 156 is shaped so lip 160 can seat in groove 148 internal to valve 146. Again in some versions of the invention, valve 146 is molded into ring 156.

Valve 146 and ring 156 are seated in the proximal end base of bore 42. More particularly, the valve 146 and ring 156 are seated in bore 66 internal to hub 58.

Delivery assembly 160 functions in the same general manner in which the first described delivery assembly 20 functions. Unless a stylet or a delivery cannula 82 is seated in access cannula 142, valve flaps 150 abut so as to place the valve in the closed state. Valve 146 thus prevents the flow of material out of the access cannula. The insertion of the stylet or delivery cannula 52 into the cannula handle 24 provides sufficient force to flex the valve flaps 150 inwardly. This flexing of the valve flaps opens the valve 146.

When the delivery cannula 82 is disposed in the access cannula there may be times when a head of pressure develops at the site at which the distal end of the assembly 160 is located. This pressure may urge delivery cannula 82 proximally outwardly. If this event occurs, the valve flaps 150 move, flex proximally, with the cannula. The valve flaps flex into the annular space in fitting bore 41 around the delivery cannula 82. Owing to the dimensions of the components, the valve flaps 150 are compressed against the tube 94 integral with the delivery cannula 82. This compressive force is typically greater than force of the fluid that is pushing the delivery cannula 82 outwardly. Thus valve 150 of this version of the invention, further functions as a brake that stops pressure generated at the site to which the assembly is applied from forcing the delivery cannula 82 out of the access cannula when such movement is not desired.

The manual force a practitioner applies to the delivery cannula 82 to withdraw the delivery cannula from the access cannula 142 is sufficient to overcoming the braking force the valve applies to the cannula tube 94 to inhibit unintended retraction of the delivery cannula 82.

Figure 8:
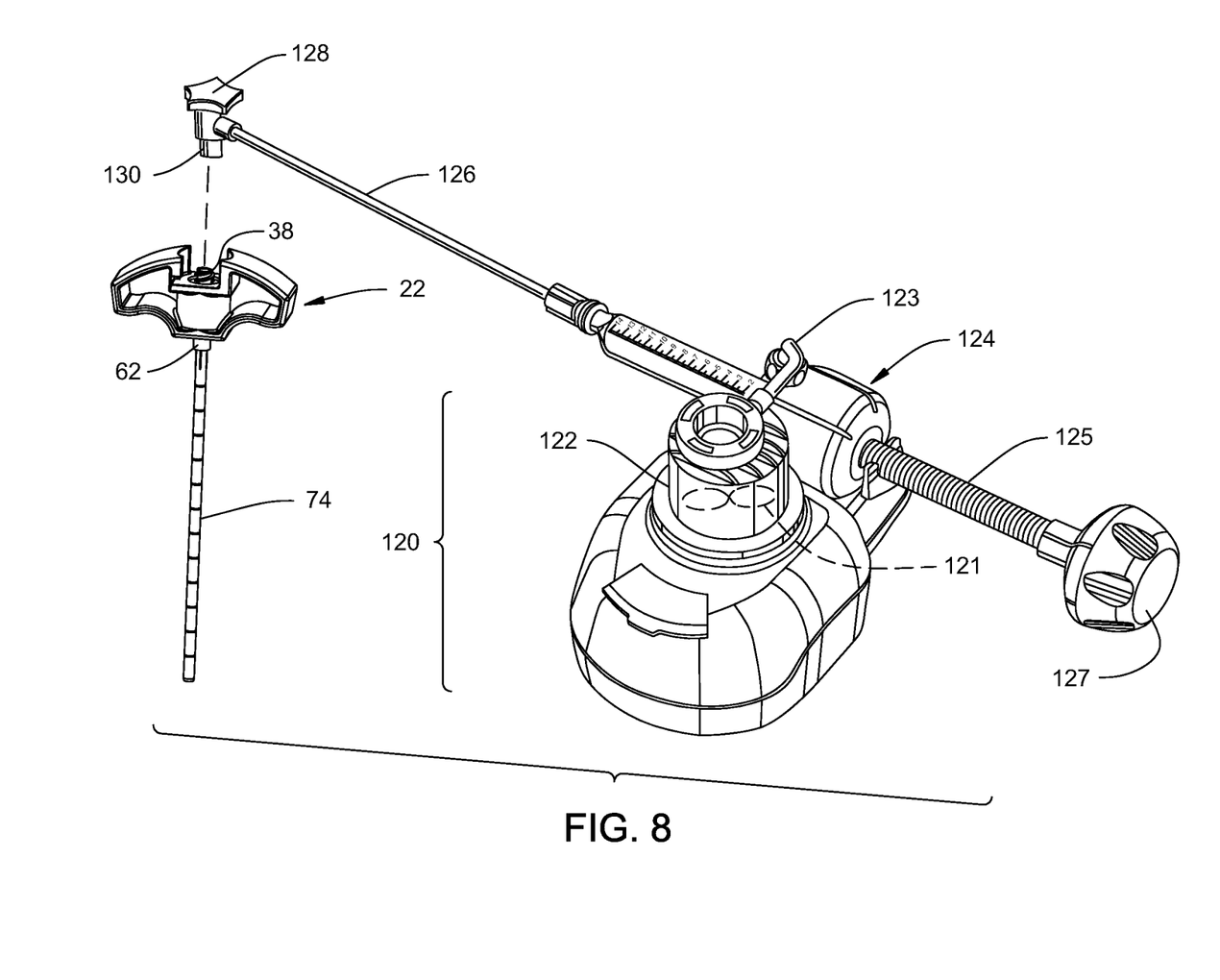
FIG. 8 depicts an alternative cement mixer and cement delivery assembly of this invention.

FIG. 8 illustrates another assembly of this invention. Here access cannula 22 is connected directly to cement mixer 120. In this version of the invention, access cannula fitting 38 is adapted to be releasably attached to mixer outlet fitting 130. Thus this version of the assembly of this invention does not include a delivery cannula. In this version of the invention, the access cannula is typically attached filled with cement after the cannula is positioned adjacent the tissue into which the cement is to be flowed.

In this version of the invention, valve 48 (FIG. 2) is still normally closed. The valve 48 prevents back flow of fluid out of the access cannula when neither the stylet nor obturator are fitted in the cannula 22. It should be appreciated that in this version of the pressure applied when the cement is forced through the cement mixer by piston 125, is sufficient to open up the valve. When this pressure is released, the elastomeric force of the valve returns the valve to the closed state.

It should be understood that the foregoing is directed to specific versions of the delivery assembly of this invention. Other versions of the assembly may have features different from what has been described.

For example, it should be clear from the text, that the assembly of this invention can be employed to deliver fluids and semi-solids into living tissue other than bone cement. Generally this means that cannula 82, the cannula disposed in the access cannula can be called a delivery cannula. Thus the structure of the fitting of the delivery cannula 82 may be specific to the fill device employed to load the cannula with the material to be injected into the tissue.

The structure of the handles integral with cannulae 22 and 82 is understood to be exemplary, not limiting. Likewise, some access cannulae and delivery cannulae of this invention may have additional components that, when employed create the void space into which the material that is inject is to be injected.

Further, this invention is not limited to valves wherein the moving valve elements are one or more elastomeric flaps. In some versions of the invention, the valve may be a mechanical valve. This valve for example could be a flapper valve. A spring normally holds the valve element closed. When a stylet, a void creation tool or a delivery cannula is inserted in the access cannula the force of the insertion overcomes the spring force so as to pivot the valve open. The actual valve element would pivot distally to an open. Another valve of this invention may be a duck-billed valve.

Other elastomeric devices than the disclosed planar member may alternatively function as the valve elements of the valve. In one such assembly, the valve element is planar. The valve element is formed with a relatively small opening that is normally closed. The insertion of stylet, a delivery cannula or an obturator into the access cannula provides enough force against the valve to force the dilation of the valve so that the opening expands in diameter from the closed state to an open state. In still other versions of the invention, the valve is toroidal in shape. The inner surfaces of the material forming the valve normally abut so as to hold the valve in the closed shape. The force of the stylet, the delivery cannula or obturator against the inner surface of the valve element causes the radially outward compression of the valve element. In other words, the valve element is dilated open. In both these versions of the invention the pressure head of the fluid that may be directed proximally within the access cannula is not sufficient to force the valve element into the open state.

Dimensions, unless recited in the claims, are understood to be exemplary, not limiting.

Accordingly, it is an object of the appended claims to cover all such variations and modifications that come within the true spirit and scope of the invention.

What is claimed is:

1. An access cannula for preventing leakage of material, the cannula comprising:
   a tube formed from material capable of being inserted into a living body, said tube having opposed proximal and distal ends, the distal end of the tube configured for insertion into the living body and said tube defining a lumen that extends through the tube;

a valve attached adjacent the proximal end of said tube, said valve having at least one element that is normally closed over said tube to prevent the proximal flow of material out of said tube and that is capable of moving to an open position upon the manual insertion of a delivery cannula in the access cannula and a biasing member that, upon removal of the delivery cannula from the tube, returns the at least one element to the closed position; and a handle having a proximal bore and a distal bore and said valve is mounted in said handle so as to be between said proximal bore and said distal bore, at least one of said proximal bore and said distal bore having a diameter greater than the lumen of said tube.

2. The access cannula of claim 1, wherein said valve is further constructed so that, during removal of the delivery cannula from said tube, said at least one valve element is configured to press against the delivery cannula to inhibit retraction of the delivery cannula from the access cannula tube.

3. The access cannula of claim 1, wherein:
said valve is positioned so that when said at least one valve element moves between the closed and open positions, said at least one valve element is disposed only within said handle.

4. The access cannula of claim 1, wherein:
during insertion of the delivery cannula into said tube, said at least one valve element is configured to pivot into said handle distal bore; and
during removal of the delivery cannula from said tube, said at least one valve element is configured pivot into the proximal bore.

5. The access cannula of claim 1, wherein said at least one valve element is formed from elastomeric material so that said valve element functions as said biasing member that urges said valve element into the closed position.

6. The access cannula of claim 1, wherein said valve is a planar member formed from elastomeric material that has at least one slit, said slit defining said at least one flap, said flap being said at least one valve element.

7. The access cannula of claim 6, wherein said valve is formed with plural slits so as to define plural said valve flaps.

8. The access cannula of claim 6, wherein said valve is disc-shaped.

9. The access cannula of claim 6, wherein said valve is disposed in a ring that circumferentially surrounds said valve.

10. The access cannula of claim 6, wherein said valve includes four said valve flaps.

11. An access cannula for preventing leakage of material, the cannula comprising:
a tube formed from material capable of being inserted into a living body, said tube having opposed proximal and distal ends, the distal end of the tube configured for insertion into the living body and said tube defining a lumen that extends through said tube;

a valve attached adjacent the proximal end of said tube, said valve having at least one element that is normally closed over said tube to prevent the proximal flow of material out of said tube and that is capable of moving to an open position upon the manual insertion of a delivery cannula in said tube; and a handle having a proximal bore and a distal bore, said valve is mounted in said handle so as to be between said proximal bore and said handle distal bore, at least one of said proximal bore and said distal bore having a diameter greater than said lumen of said tube.

12. The access cannula of claim 11, wherein said valve is further constructed so that, during removal of the delivery cannula tube from said tube, said at least one valve element is configured to press against the delivery cannula to inhibit retraction of the delivery cannula from said tube.

13. The access cannula of claim 11, wherein:
said valve is positioned so that when said at least one valve element moves between the closed and open positions, said at least one valve element is disposed only within said handle.

14. The access cannula of claim 11, wherein:
during insertion of the delivery cannula into said tube, said at least one valve element is configured to pivot into said distal bore;
during removal of the delivery cannula from said tube, said at least one valve flap is configured to pivot into said proximal bore.

15. The access cannula of claim 11, wherein said at least one valve element is formed from elastomeric material so that said valve element functions as said biasing member that urges said valve element into the closed position.

16. The access cannula of claim 11, wherein said valve is a planar member formed from elastomeric material that has at least one slit, the slit defining the at least one flap, said flap being said at least one valve element.

17. The access cannula of claim 16, wherein said valve is formed with plural slits so as to define plural said valve flaps.

* * * * *